(12) United States Patent
Kim et al.

(10) Patent No.: US 6,566,529 B1
(45) Date of Patent: May 20, 2003

(54) TWO-PHOTON ABSORPTION MATERIALS BASED ON DTT

(75) Inventors: Oh-Kil Kim, Burke, VA (US); Han Young Woo, Kyonggi-Do (KR); Kie-Soo Kim, Taejon (KR); Kwang-Sup Lee, Taejon (KR)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/574,256

(22) Filed: May 19, 2000

(51) Int. Cl.$^7$ .................. C07D 413/10; C07D 413/14
(52) U.S. Cl. ................... 548/145; 548/444; 549/31
(58) Field of Search ................ 549/31; 548/143, 548/145

(56) References Cited

PUBLICATIONS

Kim, Chem. Mater. 12 (2) 284–6 2000.*

Kim, Polym. Prepr. 41(1) 795–6 2000.*

Kim, Polym. Prepr. 41(1) 800–1 2000.*

* cited by examiner

Primary Examiner—Robert Gerstl
(74) Attorney, Agent, or Firm—John J. Karasek; George A. Kap

(57) ABSTRACT

This invention pertains to DTT-based compounds having two-photon absorption property containing electron donors and/or electron acceptors and having cross section value σ that is higher than compound AF-50.

7 Claims, No Drawings

TWO-PHOTON ABSORPTION MATERIALS BASED ON DTT

BACKGROUND OF THE INVENTION

1. Field of the Invention

This invention pertains to materials exhibiting strong two-photon absorption that has optical power limiting property which property is particularly useful for protection of human eyes and sensitive photodetectors.

2. Description of Related Art

Non-linear optical materials exhibiting two-photon absorption cross section have drawn growing attention recently due to the unique feature that the two-photon absorption, in the presence of intense laser pulses, is capable of creating excited states with photon of half the normal excitation energy and this allows an enhanced penetration into absorbing media. Thus, two-photon absorption materials with a large cross section value σ have a variety of application areas, particularly as in optical power limiters.

A number of recent compounds or chromophores, including commercial dyes, display two-photon absorption but they have relatively small cross section values. Unfortunately, design criteria for molecules with large cross section values have not been developed.

A design strategy developed recently is based on the molecules consisting of a three-component system with a unique heteroaromatic π center which is linked symmetrically or asymmetrically through conjugation by electron donors D or electron acceptors A, resulting in products D-c-D, or D-c-A or A-c-A, where c represents the π center group. It is claimed that the cross section value σ can be enhanced by increasing the conjugation length, D/A strength and molecular symmetry that enhance the electronic redistribution from the electron donor ends D of the molecule to the center c, or vice versa, resulting in a large increase of the cross section value σ and the shift of the two-photon absorption peak to the longer wavelengths. In particular, when the π center c portion of the molecule has an electron-deficient substituent, D-c-D molecules become more effective.

On the other hand, one notable compound developed by the Air Force Lab, i.e., AF-50, and is known as a benchmark of cross section σ, has an asymmetric structure D-c-A where D is diphenylamine group, c is 9-dialkylfluorenyl and A is 4-ethenylpyridine. This structural formula of the AF-50 product is as follows:

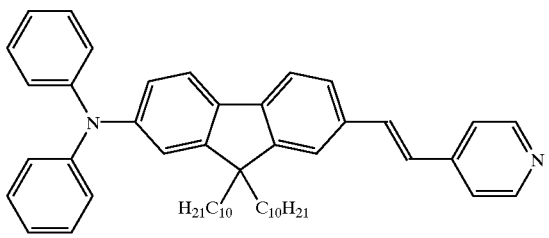

OBJECTS AND BRIEF SUMMARY OF THE INVENTION

An object of this invention is materials or compounds based on dithienylthiophene (DTT) or derivatives thereof which have the two-photon absorption property characterized by up energy conversion.

Another object of this invention is compounds containing dithienylthiophene or a derivative thereof having attached at its ends an electron donor or an electron acceptor.

Another object of this invention is compounds containing dithienylthiophene or its derivatives having attached at its ends electron donors or electron donors and electron acceptors, the compounds having a two-photon absorption property.

Another object of this invention is compounds based on dithienylthiophene or its derivatives having attached at its ends an electron donor or an electron acceptor and having a two-photon absorption property.

Another object of this invention is compounds containing dithienylthiophene or its derivatives the π center having attached at its ends electron donors and/or electron acceptors, and the compounds having two-photon absorption property with cross section value σ being in excess of about $3 \times 10^{-46}$ $cm^4$ sec when measured at 8 ns pulse duration.

DETAILED DESCRIPTION OF THE INVENTION

The present invention relates to novel organic oligomeric chromophore compounds having an outstanding nonlinear optical property of two-photon absorption. The compounds of this invention are based on dithienylthiophene or a derivative thereof having attached thereto electron donors and/or electron acceptors. These compounds exhibit greater two-photon absorption cross section σ values so that a variety of applications are expected in areas such as two-photon excited fluorescence microscopy, optical limiting, three-dimensional optical data, storage, and two-photon induced caging studies. The compounds of this invention are soluble in common organic solvents, thermally stable and form optical quality films when cast from solutions. Also, these compounds are compatible with many organic polymers and dyes, forming optical quality thin films of blends free of phase separation.

The novel compounds of this invention contain a π center based on dithienylthiophene and are conjugated. Such compounds have an outstanding nonlinear optical property of two-photon absorption as determined by cross section value σ (sigma).

The compounds of this invention having the two-photon absorption property can generally be represented as

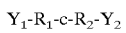

where $Y_1$ and $Y_2$ are individually selected from substituted or unsubstituted electron donors and electron acceptors, $R_1$ and $R_2$ are individually selected from conjugated hydrocarbon linkages and bonds, and c is a substituted or unsubstituted π center based on dithienylthiophene or its derivatives. In a preferred embodiment, the compounds are conjugated; both Y groups are electron donors or one Y group is an electron donor and the other is electron acceptor; the R groups are ethylene linkages each containing 2–6 carbon atoms; and the center c is a π center based on dithienlthiophene or its derivative. More specifically, the compounds of this invention can be depicted as follows:

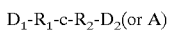

where $D_1$ and $D_2$ are individually selected from substituted or unsubstituted electron donor groups, $R_1$ and $R_2$ are individually selected from substituted or unsubstituted ethylenic linking groups, c is substituted or unsubstituted π center group based on DTT and A is a substituted or unsubstituted electron acceptor group. Suitable substituents are groups that do not adversely affect the two-photon absorption property of the compounds and include alkyl groups of $C_1$–$C_{16}$ carbon atoms, particularly at positions 3 and 3' on the dithienylthiophene group.

In an especially preferred embodiment the compounds of this invention include oligomeric solid compounds 101, 102, 103 and 104, depicted below:

thiopheno[2',3',-4,5]thiopheno[3, 2-b}thiophen-2-yl}vinyl) phenyl]diphenylamine; depicted above, the central DTT group is attached through conjugation to either an electron donor at both ends or an electron donor at one end and an electron acceptor at the other end, forming symmetrical compounds 101 and 103 or unsymmetrical compounds 102 and 104. As used herein, "D" denotes an electron donor group, "c" denotes the DTT group π centrer, and "A" denotes an electron acceptor group. The electron donor

101

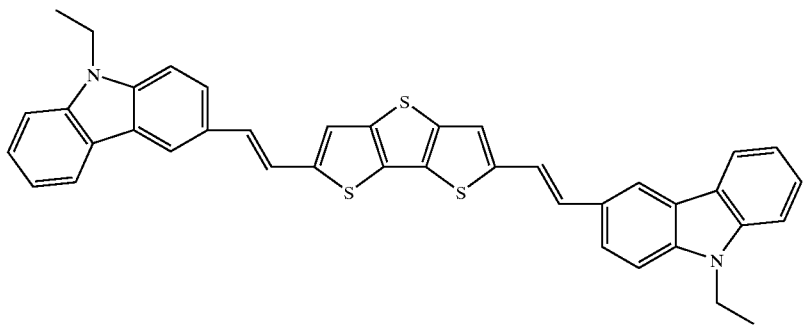

102

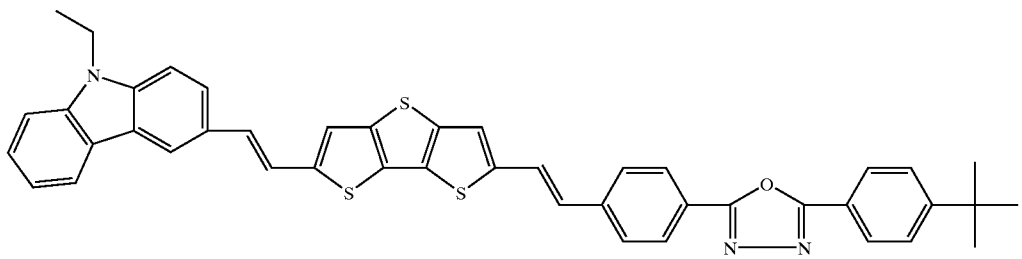

103

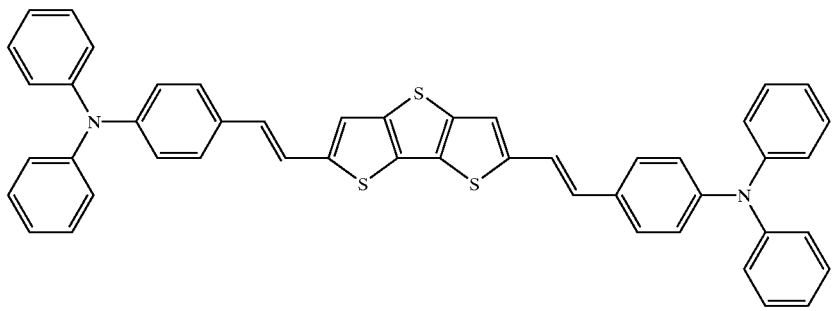

104

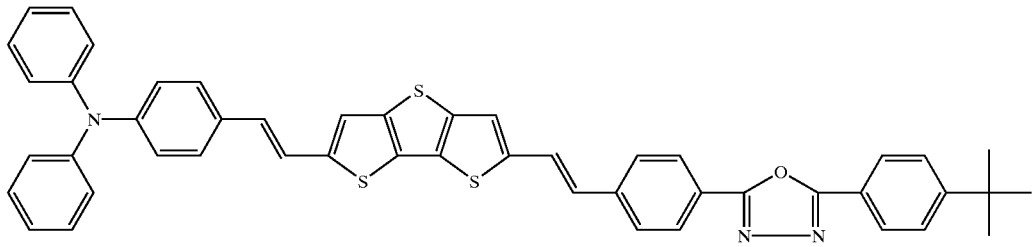

In the compounds 101, i.e., 2,6-bis[2-(9-ethylcarbazol-3-yl)vinyl]thiopheno[3',2'-2,3]thiopheno[4,5-b]thiophene; 102, i.e., 2-[2-(4-{5-[4-(tert-butyl)phenyl](1,3,4-oxadiazol-2-yl)}phenyl)vinyl]-6-[2-(9-ethylcarbazol-3-yl)vinyl] thiopheno[3',2'-2,3]theopheno[4,5-b]thiophene; 103, i.e., {4-[2-(6-{2-[4-(diphenylamino)phenyl]vinyl}thiopheno[2', 3'-4,5]thiopheno[3,2-b]thiophen-2-yl)vinyl] phenyl}diphenylamine; and 104, i.e., [4-(2-{6-[2-(4-{5-[4-(tert-butyl)phenyl](1,3,4-oxadiazol-2-yl)}phenyl)vinyl]

groups and the electron acceptor groups are connected to the central DTT-based π center by means of ethylenic linkage —CH=CH—. In a preferred embodiment, D is a carbazole or a triphenylamine group and A is a 2-mono or diparyl-5-(4-ter-butyl)-1,3, 4-oxadiazole group.

Compounds of this invention can be synthesized by the Wittig reaction of a dithienyldthiophene dicarboxaldehyde with a triphenylphosphonium functional end of D or A group. Ultrapure products can be obtained through exhaustive purficiations by column chromatography and confirmed by NMR, electronic spectrum and elemental analysis.

As shown in FIG. 1, when the compounds comprise an asymmetric D/A pair of mixed components in the molecule, as in compounds 102 and 104, above, their absorption maximum of single photon absorption, $\lambda_{max}$, is slightly red-shifted about 5 nm relative to that of their symmetric D/D pair counterpart, as in compounds 101 and 103, above. This is due to a partial charge transfer in the excited state of the asymmetric molecule. These compounds are highly fluorescing, particularly when the DTT π center group is linked by a symmetric D/D pair. The emission intensity of single photon excitation of compounds with the asymmetric structure is significantly smaller relative to the symmetric counterpart. This difference in the emission intensity is probably due to a partial quenching associated with intramolecular charge transfer.

Table I, below, gives cross-sections σ of the compounds 101, 102, 103 and 104 and cross-sections σ of the related optical limiters AF-50, BPBAS and BDPAS, for comparison purposes.

Table I, below, gives two-photon absorption cross-section values measured under nanosecond pulses for DTT-based compounds 101, 102, 103 and 104 in comparison to the other optical limiters based on fluorene and stilbene as π centers.

TABLE I

| Compound | 101 | 102 | 103 | 104 | AF-50[a] | BDBAS[b] | BDPAS[c] |
|---|---|---|---|---|---|---|---|
| Solvent | TCE | TCE | TCE | TCE | Benzene | Acetone | Toluene |
| Concentration ($10^{-2}$ mol/L) | 0.74 | 0.91 | 0.97 | 0.74 | 4.5 | 5 | 5 |
| Wavelength (nm) | 810 | 810 | 810 | 810 | 800 | 600 | 700 |
| Pulse Duration (ns) | 8 | 8 | 8 | 8 | 8 | 5 | 5 |
| NL Abs. Coeff. β (cm/GW) | 19 | 7.5 | 47 | 19 | 21 | — | — |
| σ ($10^{-20}$ cm$^4$/GW) | 428 | 136 | 810 | 483 | 78 | — | — |
| σ ($10^{-46}$ cm$^4$ sec) | 10.5 | 3.35 | 19.9 | 11.9 | 1.94 | 1.77 | 1.30 |

[a]N,N-Diphenyl-7-[2-(4-pyridinyl)ethenyl]-9,9-di-n-decylfluorene-2-amine.
[b]4,4'-bis(di-n-butylamino)stilbene
[c]4,4'-bis(diphenylamino)stilbene.

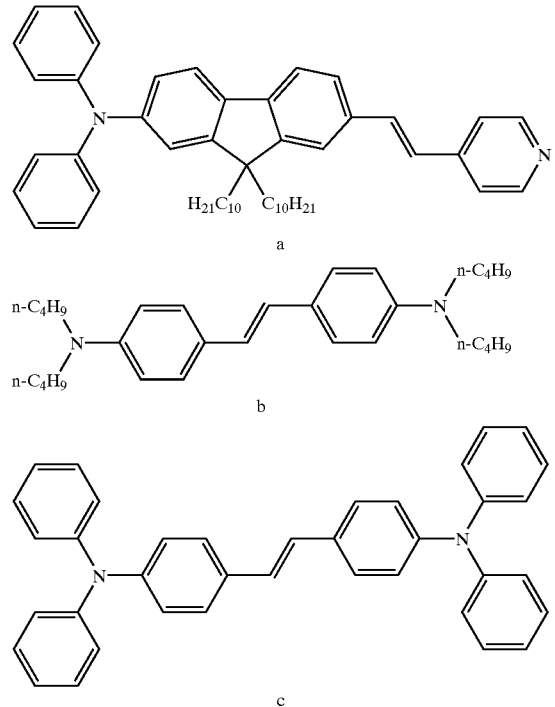

The two-photon absorption cross-section values σ were determined from experimentally measured two-photon absorption coefficient β, which was obtained by measuring the nonlinear transmissivity $T_i$ of the compounds in solution for a given input intensity $I_0$ and a given thickness of a sample solution $l_0$, from the following relationship:

$$T_i = [1n(1+\beta 1_0 I_0)/\beta 1_0 I_0]$$

$$\sigma = h\nu\beta/N_0 = 10^3 h\nu\beta/N_A c$$

where $N_0$ and $N_A$ are the density of assumed absorptive centers and Avogadro's number, respectively, and c is the molar concentration of the solute.

The β values of the DTT-based compounds 101, 102, 103 and 104 were measured in tetrachloroethane using 810 nm and 8 ns pulse laser beam at the intensity level of several hundred of megawatt per square centimeter.

There are significant differences in the cross-section values σ of the compounds, depending on the structural variations. The symmetric structure of compoundes 101 and 103 exhibits relatively larger values compared to the respective asymmetric compounds 102 and 104, and the stronger electron donor triphynylamine groups compared to N-ethylcabazole groups seems to be more effective. When a comparison is made among the tested compounds differing in the π-center, the cross section values σ of DTT-based compounds are about 2–10 times larger than for compounds based on fluorene and stilbene. When the comparison is made with respect to the asymmetric compounds 102 and 104, with nearly comparable strength of the A groups, i.e., pyridine vs. oxadiazole groups, the cross-section value σ of compound 104 is about six times larger than that of the compound AF-50. The cross-section value σ of DTT-based asymmetric compound 104, for example, is much larger than that of symmetric stilbene-based compounds BDBAS and BDPAS.

It is worth noting that there is no marked difference in cross-section values between symmetric and asymmetric structures of the compounds 103 and 104, for example. This seems to suggest that the importance of structural symmetry may be a valid argument for the larger cross-section values σ but even more important is electronic properties of individual groups and their combination, as indicated in compounds 101 and 104. The cross-section σ of compound 104 with an asymmetric structure is even larger than that of compound 101 with a symmetric structure.

Measurement of the cross-section values σ is made in a good solvent. The fact that a different solvent is used will not appreciably affect the cross section values σ as long as a good solvent for the particular compound is used. Likewise, concentration does not appreciably affect determination of the cross-section values σ.

For comparison, additional two-photon absorption measurements were carried out at 160 femtosecond using a 796 nm pulsed laser in an irradiance range of 0–20 gigawatt per square centimeter. Both nanosecond and femtosecond Z-scan methods were used to investigate the effect of pulse width and hence the relative contribution of excited state absorption to the two-photon absorption.

Table II, below, summarizes the cross-section values measured with femtosecond pulses for compound 103 and compound AF-50.

TABLE II

| Chromophore | 103 | AF-50 |
| --- | --- | --- |
| Solvent | TCE | Benzene |
| Concentration ($10^{-2}$ mol/L) | 0.5 | 4.5 |
| Wavelength (nm) | 796 | 796 |
| Pulse Duration (fs) | 160 | 160 |

TABLE II-continued

| Chromophore | 103 | AF-50 |
| --- | --- | --- |
| Irradiance Range (GW/cm$^2$) | Up to 20 | Up to 20 |
| σ' ($10^{-20}$ cm$^4$/GW) | 1.1 | 0.12 |
| σ ($10^{-48}$ cm$^4$ sec) | 2.7 | 0.30 |

When compared with the nanosecond measurement values, femtosecond values were about 2–3 orders of magnitude lower. However, even under the femtosecond measurement, the two-photon cross-section value of compound 103 is nearly one order of magnitude greater relative to the compound AF-50, as is also evident from the nanosecond measurements.

The distinct role of the DTT control groups in the compounds of this invention, relative to the two-photon absorptivity, may be associated with the unique electronic properties of the rigid, planar fused terthiophene structure which contributes a great deal to the reduction of band gap and the extended π electron delocalization, where sulfur d-orbitals are effectively mixing with π electrons. In related applications, it was determined that properties of DTT, as an electron relay in push-pull nonlinear compounds, were significantly more efficient as compared to phenyls and other oligothiophenes.

Having described the invention, the following examples are given as particular embodiments thereof to demonstrate preparation of the DTT-based compounds. It is understood that the examples are given by way of illustration and are not intended to limit the specification or the claims in any manner.

EXAMPLES

Synthesis of dithienophene-bearing or DTT-bearing compounds was carried out by formylation (DTT-2CHO) of DTT and subsequent Wittig reactions with electron donor D and/or electron acceptor A component. The DTT-2CHO, i.e., dithieno[3,2-b:2',3'-d]thiophene-2,6-dicarboxaldehyde, prepared by treatment of DTT with N-BuLi, and then with dimethylformamide (DMF), underwent the coupling reaction with a triphenylphosphonium functional end of D or A moiety. During the coupling reaction of DTT-2CHO with D (or A), a monofunctional D-(or A-)DTT-CHO was formed as a byproduct. This was separated/purified and used for the synthesis of asymmetric compounds or dyes. Procedure for the synthesis of symmetric and asymmetric dyes 101, 102, 103 and 104 are given below:

Example 1

Preparation of Compound #101

Compound #101 was prepared in accordance with the following process:

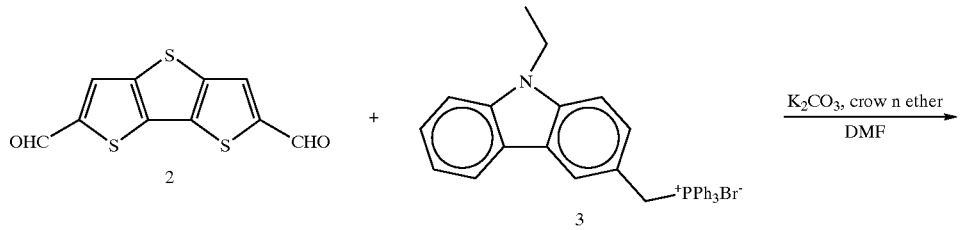

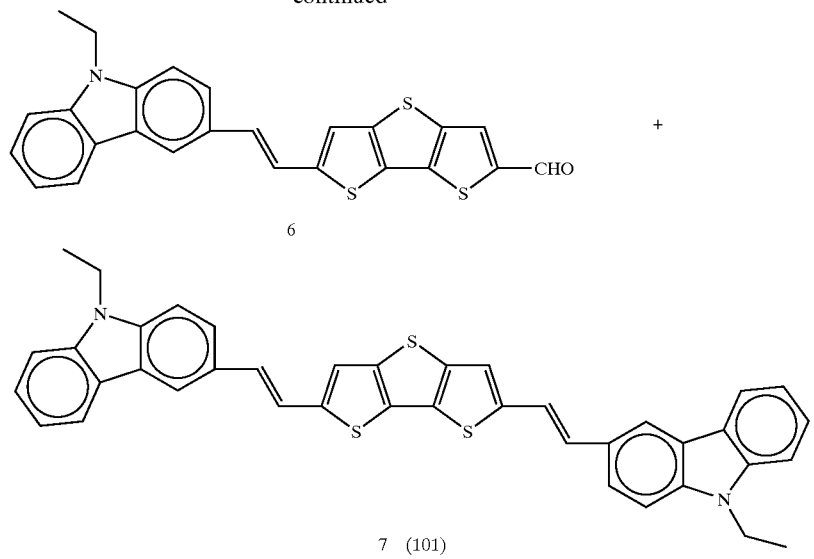

To the mixture of compound 2 (0.5 g, 1.98 mmol), potassium carbonate (1.37 g, 9.91 mmol), and a catalytic amount of about 5 mg of crown ether in 40 mL of anhydrous DMF was added compound 3 (2.40 g, 4.36 mmol) in 45 mL of DMF dropwise. The solution was stirred overnight at room temperature. The resulting solution was poured into cold water dropwise to give an orange solid. The precipitated orange solid was filtered off and dried over $P_2O_5$ in vacuum at 50 C. The crude product was purified by column chromatography (eluent, MC:hexane=1:1 (v/v)) and recrystallization from methylene chloride (MC). The brown needle-shaped crystal (0.68 g, 54.0%) was obtained. $^1$H-NMR (CDCl$_3$, ppm): δ 8.19 (s, 2H, Ar H), 8.12 (d, 2H, Ar H), 7.63 (d, 2H, Ar H), 7.46 (m, 2H, Ar H), 7.36 (m, 4H, Ar H), 7.32–7.11 (m, 8H, Ar H), 4.36 (q, 4H, —NCH$_2$CH$_3$), 1.44 (t, 6H, —NCH$_2$CH$_3$).

Example 2

Preparation of Compound #102

Compound #102 was prepared in accordance with the following process:

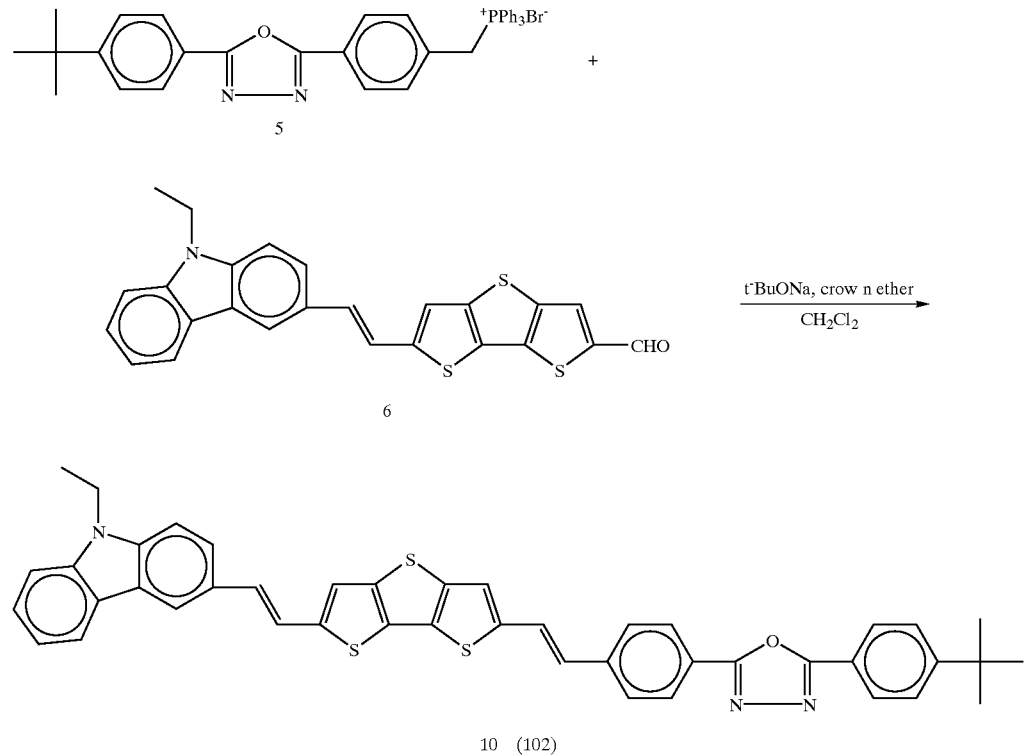

Compound 6 (0.5 g, 1.13 mmol) was dissolved in 30 mL of anhydrous MC. Sodium tert-butoxide (0.22 g, 2.29 mmol) and a catalytic amount of about 5 mg of crown ether were added to the solution. It was stirred until compound 6 was completely dissolved. Compound 5 in 20 mL of MC was added dropwise at room temperature and the resulting solution was stirred for 5 hours. After the precipitated fine particle was removed out by filtration, the solution was washed with water several times. The organic portion was concentrated under reduced pressure to yield an orange solid. The pure product was obtained by column chromatography (eluent, chloroform/ethyl acetate). The product yield was 0.3 g (37.5%). $^1$H-NMR (CDCl$_3$, ppm): δ 8.13–7.98 (m, 6H, Ar H), 7.53–7.48 (m, 6H, Ar H), 7.33 (m, 3H, Ar H), 7.27–7.08 (m, 5H, Ar H), 6.85 (d, 1H, Ar H), 4.30 (q, 2H, —NCH$_2$CH$_3$), 1.40 (t, 3H, —NCH$_2$CH$_3$), 1.35 (s, 9H, —C(CH$_3$)$_3$).

To the mixture of compound 2 (0.50 g, 1.98 mmol), potassium carbonate (0.55 g, 3.9 mmol), and a catalytic amount (about 5 mg) of crown ether was added 30 mL of anhydrous DMF. Compound 4 (1.19 g, 1.98 mmol) in 30 mL of anhydrous DMF was added dropwise to the above solution. After the resulting mixture was stirred for 4 hours at room temperature, it was poured into cold water dropwise with vigorous stirring. The precipitated orange solid was filtered off and dried under vacuum at 60° C. The pure compound (0.33 g, 33.7%) was obtained by silica gel column chromatography (MC:hexane=1:1 (v/v)). One of the final products, compound 9, was also yielded as a byproduct (0.12 g). $^1$H-NMR (δ, CDCl$_3$, ppm): δ 9.91 (s, 1H, —CHO), 7.90 (s, 1H, Ar H), 7.35–7.20 (m, 5H, Ar H), 7.19–6.92 (m, 12H, Ar H).

Example 3

Preparation of Compound #103

Compound #103 was prepared in accordance with the following process:

Example 4

Preparation of Compound #104

Compound #104 was prepared in accordance with the following process:

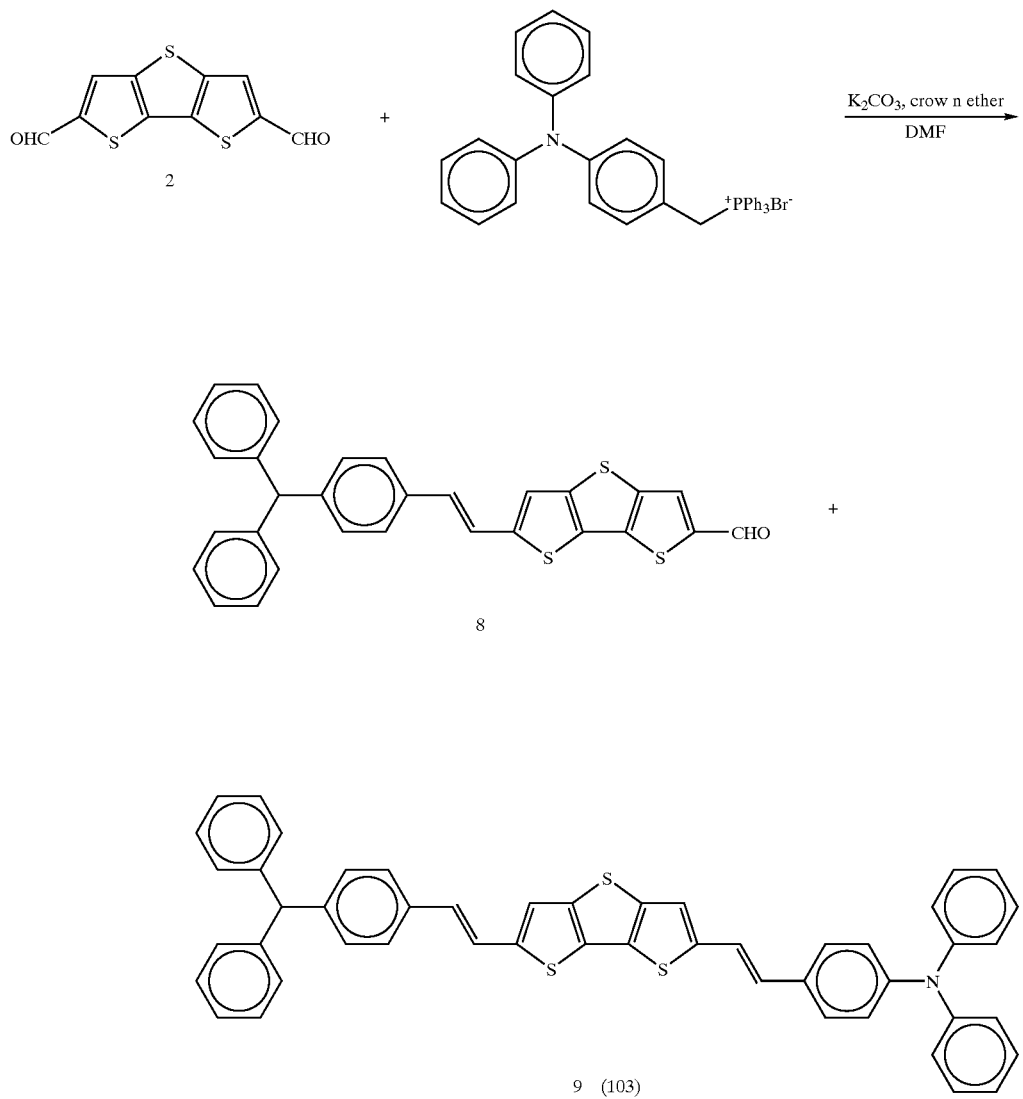

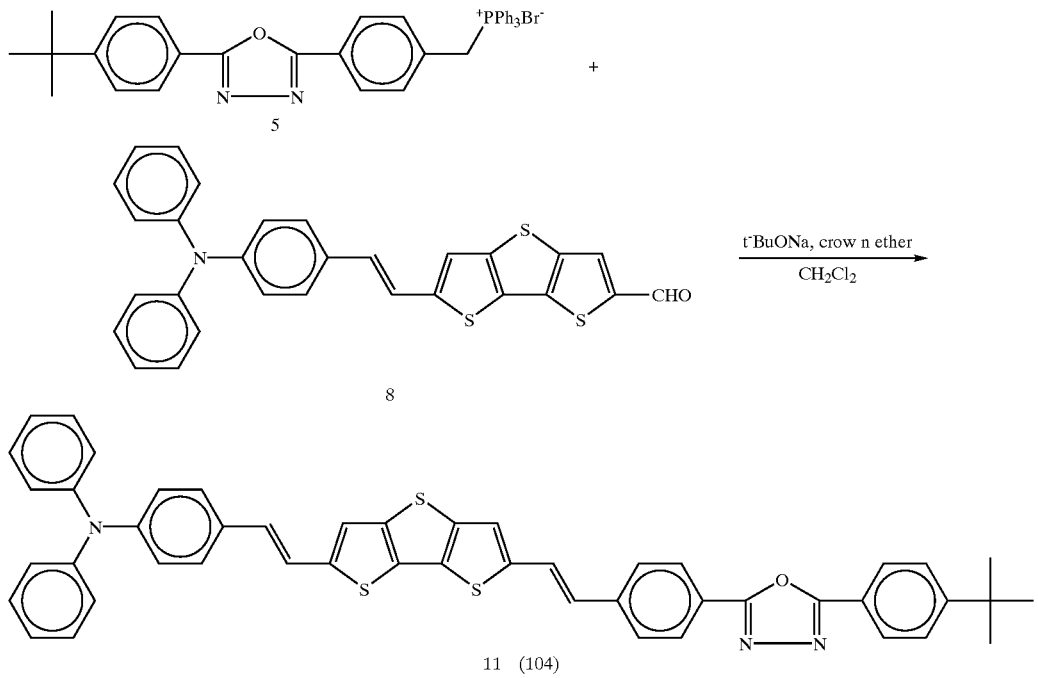

Compound 8 (0.30 g; 0.61 mmol) was dissolved in 20 mL of anhydrous MC. Sodiumtert-butoxide (0.12 g, 1.25 mmol) and a catalytic amount of about 5 mg of crown ether were added to the solution. It was stirred until compound 8 was completely dissolved. Compound 5 (0.39 g, 0.61 mmol) in 20 mL of MC was added dropwise at room temperature and the resulting solution was stirred for 5 hours. After the precipitated fine particle was removed out by filtering, the solution was washed with water several times. The organic portion was concentrated under reduced pressure to yield an orange solid. The pure product was obtained by column chromatography (eluent, chloroform/ethyl acetate). The product yield was 0.15 g (32.1%). $^1$H-NMR (CDCl$_3$, ppm): δ 8.09 (d, 2H, Ar H), 8.05 (d, 2H, Ar H), 7.60 (d, 2H, Ar H), 7.53 (d, 2H, Ar H), 7.40–7.23 (m, 7H, Ar H), 7.15–7.10 (m, 6H, Ar H), 7.08–7.01 (m, 5H, Ar H), 6.87 (d, 2H, Ar H), 1.36 (s, 9H, —C(CH$_3$)$_3$).

While presently preferred embodiments have been shown of the novel compounds having the two-photon absorption property, and of the several modifications discussed, persons skilled in this art will readily appreciate that various additional changes and modifications may be made without departing from the spirit of the invention as defined and differentiated by the following claims.

What is claimed:

1. A compound having the formula:

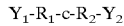

$Y_1$-$R_1$-c-$R_2$-$Y_2$ wherein $Y_1$ is selected from the group consisting of carbazole groups triphenylamine groups and mixtures thereof; and $Y_2$ is selected from oxadiazole groups: $R_1$ and $R_2$ are individually selected from conjugated ethylenic linkages containing up to 6 carbon atoms; and c is dithienylthiophene or its derivative.

2. The compound of claim 1 wherein each $R_1$ and $R_2$ is ethylenic linkage —CH═CH—.

3. The compound of claim 1 based on dithienylthiophene which is conjugated and has cross section value σ in excess of 3×10$^{-46}$ cm$^4$ sec, when measured at wavelength of about 810 nm and a pulse duration of about 8 ns.

4. The compound of claim 1 wherein $Y_1$ is selected from the group consisting of lower alkyl carbazole groups.

5. The compound of claim 4 having cross section value σ in excess of about 2×10$^{-48}$ cm$^4$ sec, when measured at wavelength of about 796 nm and a pulse duration of about 160 fs.

6. The compound of claim 5 wherein $Y_1$ is selected from the group consisting of 9-lower alkyl carbazole groups and triphenylammine groups.

7. The compound of claim 6 wherein $Y_1$ is selected from the group consisting of 9-ethyl carbazole groups and triphenylamine groups; and $Y_2$ is selected from the group consisting of 2-monoaryl or diaryl-5-(4-ter-lower alkyl)-1,3,4-oxadiazole groups.

* * * * *